United States Patent
Baba et al.

(10) Patent No.: US 11,002,744 B2
(45) Date of Patent: May 11, 2021

(54) APPARATUS AND METHOD FOR GLYCOPEPTIDE ANALYSIS

(71) Applicant: DH Technologies Development Pte. Ltd., Singapore (SG)

(72) Inventors: Takashi Baba, Richmond Hill (CA); Yves Le Blanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 16/626,732

(22) PCT Filed: Jun. 28, 2018

(86) PCT No.: PCT/IB2018/054823
§ 371 (c)(1),
(2) Date: Dec. 26, 2019

(87) PCT Pub. No.: WO2019/003188
PCT Pub. Date: Jan. 3, 2019

(65) Prior Publication Data
US 2020/0116733 A1   Apr. 16, 2020

Related U.S. Application Data

(60) Provisional application No. 62/525,901, filed on Jun. 28, 2017.

(51) Int. Cl.
*G01N 33/68* (2006.01)
*H01J 49/00* (2006.01)
(Continued)

(52) U.S. Cl.
CPC ...... *G01N 33/6848* (2013.01); *H01J 49/0072* (2013.01); *H01J 49/022* (2013.01); *H01J 49/4225* (2013.01)

(58) Field of Classification Search
CPC .............. G01N 33/6848; H01J 49/0072; H01J 49/022; H01J 49/4225
See application file for complete search history.

(56) References Cited

U.S. PATENT DOCUMENTS

2014/0374592 A1   12/2014   Baba
2015/0144783 A1   5/2015    Murase
2015/0160232 A1   6/2015    Chen et al.

FOREIGN PATENT DOCUMENTS

WO   2014191821 A1   12/2014
WO   2016020789 A1   2/2016

OTHER PUBLICATIONS

International Search Report and Written Opinion for PCT/IB2018/054823 dated Oct. 31, 2018.

*Primary Examiner* — Nicole M Ippolito
*Assistant Examiner* — Hanway Chang

(57) ABSTRACT

A system and method is described for characterizing glycopeptides which includes a first quadrupole mass filter, a multipole rod set of an ion guide, a lens electrode, an ExD device and a mass analyzer. The multipole rod set is adapted to receive a radial radio frequency (RF) trapping voltage and a radial dipole direct current (DC) voltage The lens electrode is adapted to receive an axial trapping alternating current (AC) voltage and a DC voltage. The ExD device performs electron capture dissociation or electron transfer dissociation, the ExD device being positioned so that an entrance of the ExD device is disposed on the other side of the lens electrode opposite the multipole rod set. The mass analyzer is positioned at an exit of the ExD device for receiving ions from the ExD device.

14 Claims, 6 Drawing Sheets

(51) Int. Cl.
*H01J 49/02* (2006.01)
*H01J 49/42* (2006.01)

APPARATUS AND METHOD FOR GLYCOPEPTIDE ANALYSIS

CROSS REFERENCE TO RELATED APPLICATION

This application claims priority to U.S. provisional application No. 62/525,901 filed on 2017 Jun. 28 the content of which is incorporated herein by reference in its entirety.

FIELD OF THE INVENTION

The teachings described herein are directed to glycopeptide analysis using mass spectrometry and apparatuses and methods to achieve same.

BACKGROUND

Glycopeptides are a class of peptide structures that comprise one or more carbohydrate moieties that are covalently bonded to side chains of the amino acid residues that make up the peptide. In several cases, the glycans form a backbone of sugar moieties. Glycopeptides are classified depending on the linkage between the glycan portion (ie, the carbohydrate) and the amino acid residue. In addition, linkage between glycan moieties is also important.

Glycopeptides can be characterized in a limited way using conventional mass spectrometry. Tandem mass spectrometry using collision induced dissociation (CID) can break glycosidic bonds and can be utilized to analyze the glycan portion of the molecule which can include the ordering and identity of the component sugars moieties. In other cases, CID can be used to sequence the peptide region.

Electron based dissociation (referred to generically as ExD herein) which can include electron transfer dissociation (ETD), and various forms of Electron capture dissociation (ECD), such as Hot ECD, can be used for various purposes which can include the sequencing of the peptide portion of the molecule and to identify the site of glycosylation, for example, determination of the site of linkage (e.g., 2, 3, 4 or 6 position) of a monosaccharide. In the latter case, identifying the site of glycosylation can only be performed on glycans that have been released from the peptide, typically by usage of enzyme cleavage. These electron based dissociation methods perform cross-ring cleavage of the sugar rings which allows linkage positions to be determined in subsequent analysis. The identification of linkage position cannot be utilized on glycopeptides themselves (absent the pre-separation of the glycans from the peptides through for example, enzyme cleavage) because electron based dissociation methods performed on intact glycopeptides preferentially disassociate the peptide chains rather the glycan rings.

It is therefore desirous to have techniques and apparatuses that are capable of characterizing glycopeptides in a more thorough manner, which can include identifying the peptide sequence, glycosylated site, glycan components and linkage of each mono-saccharide in a simplified manner.

SUMMARY

According to various embodiments, a system for mass spectrometer analysis is described which comprises: a first quadrupole mass filter; a multipole rod set of an ion guide to receive ions from the first quadrupole mass filter, the multipole rod set adapted to receive a radial radio frequency (RF) trapping voltage and a radial dipole direct current (DC) voltage. The system also comprises a lens electrode of the ion guide positioned at one end of the multipole rod set to extract ions trapped by the multipole rod set and adapted to receive an axial trapping alternating current (AC) voltage and a DC voltage, an ExD device adapted to perform electron capture dissociation or electron transfer dissociation, the ExD device being positioned so that an entrance of the ExD device is disposed on the other side of the lens electrode opposite the multipole rod set. In addition, a mass analyzer is positioned at an exit of the ExD device for receiving ions from the ExD device. A processor in communication with the multipole rods set and the lens electrode that simultaneously applies a radial dipole DC voltage to the multipole rod set and an axial trapping AC voltage to the lens electrode or simultaneously applies a radial RF trapping voltage amplitude to the multipole rode set and an axial trapping AC voltage to the lens electrode in order to extract a bandpass mass range of ions trapping in the multipole rod set. In some embodiments, the mass analyzer can comprise a time-of flight mass spectrometer, an ion trap or one or more quadrupole mass filters.

In some embodiments, the ExD device operates in at least one of two modes, wherein in one mode the ExD device functions as an ion guide and wherein in the second mode, the ExD device performs electron capture dissociation or electron transfer dissociation.

According to various embodiments, a method of analyzing a sample containing one or more glycopeptides is described, the method comprising: ionizing the sample to form glycopeptide ions, isolating one or more glycopeptide ions in a mass filter, fragmenting the isolated glycopeptide ions in a multipole rod set of an ion guide, the multipole rod set having an entrance end and an exit end, the entrance end receiving fragmented glycopeptide ions from the mass filter, the multipole rod set adapted to receive a radial radio frequency (RF) trapping voltage and a radial dipole direct current (DC) voltage, the ion guide having a lens electrode positioned at the exit end of the multipole rod set to extract ions trapped by the multipole rod set and adapted to receive an axial trapping alternating current (AC) voltage and a DC voltage, extracting a bandpass range of ions of the fragmented glycopeptide ions from the exit end of the ion guide into an ExD device by simultaneously applying a radial dipole DC voltage to the multipole rod set and axial trapping AC voltage to the lens electrode or simultaneously applying a radial RF trapping voltage amplitude to the multipole rod set and an axial trapping AC voltage to the lens electrode; performing an electron dissociation reaction or electron transfer reaction of the bandpass range of ions in the ExD device to form ExD product ions, mass analyzing the ExD productions.

In some embodiments, ionizing the sample to form glycopeptide ions comprises metalizing the one or more glycopeptides, which can include, for example, reacting the glycopeptides with a sodium salt.

In some embodiments, the extracting a bandpass range of ions is performed by simultaneously applying a radial dipole DC voltage to the multipole rod set and axial trapping AC voltage to the lens electrode and the radial dipole DC voltage and the AC voltage are selected so as to extract only glycan fragments having a range of pre-selected m/z values.

In some embodiments, the extracting a bandpass range of ions is performed by simultaneously applying a radial RF trapping voltage amplitude to the multipole rod set and an axial trapping AC voltage to the lens electrode and the RF trapping voltage amplitude and the AC voltage are selected so as to extract only glycan fragments having a range of pre-selected m/z values.

In various embodiments, a method of analyzing a glycopeptide in a sample is described which comprises: providing a mass filter, providing a multipole rod set of an ion guide, providing an ExD device positioned downstream of the multipole rod set, the ExD device adapted to operate in at least one of two modes, wherein in one mode the ExD device functions as an ion guide and wherein in the second mode, the ExD device performs electron capture dissociation or electron transfer dissociation, providing a mass analyzer positioned downstream of the ExD device; providing a lens electrode positioned between the multipole rod set and the ExD device; ionizing the sample to form metallized sample ions, transmitting the metallized sample ions to the mass filter, operating the mass filter to selectively transmit glycopeptide ions having a preselected m/z range into the multipole rod set of an ion guide, configuring the multipole rod set to operate as a collision cell with the collision cell operating at a first dissociation energy to cause formation of peptide fragments, and configuring the ExD device to operate as an ion guide, so as to transmit the formed peptide fragments through the ExD device to the mass analyzer, and analyzing the peptide fragments in the mass analyzer, configuring the multipole rod set to operate as a collision cell at a second dissociation energy to cause the formation of glycan fragments, the second dissociation energy being higher than the first dissociation energy, and configuring the ExD device to operate as an ion guide, so as to transmit the formed glycan fragments through the ExD device to the mass analyzer, and analyzing the glycan fragments in the mass analyzer. The method also includes extracting a bandpass range of glycan fragment ions from the multipole rod set into the ExD device by simultaneously applying a radial dipole DC voltage to the multipole rod set and axial trapping AC voltage to the lens electrode or simultaneously applying a radial RF trapping voltage amplitude to the multipole rod set and an axial trapping AC voltage to the lens electrode, the bandpass range of glycan fragments being defined by a pre-selected range of m/z values and configuring the ExD device to operate as an electron transfer reaction device or electron dissociation device, and performing an ExD reaction on the bandpass range of glycan fragment ions to form ExD product ions, and mass analyzing the ExD product ions.

In some embodiments, the ExD described in the methods and systems above comprises: a first set of electrodes at least a first segment of which is arranged in a quadrupole orientation about a first central axis, wherein said first segment of the first set of electrodes extends axially along said first central axis from a proximal inlet end to a distal end so as to define a first portion of a first pathway extending along said first central axis, said proximal inlet end for receiving the bandpass range of ions from the exit end of the ion guide; a second set of electrodes at least a first segment of which is arranged in a quadrupole orientation about the first central axis so as to define a second portion of the first pathway, wherein said first segment of the second set of electrodes extends axially along said first central axis from a proximal end to a distal outlet end, the proximal end of the second set of electrodes being spaced apart from the distal end of the first set of electrodes such that a transverse pathway extends between the proximal end of the second set of electrodes and the distal end of the first set of electrodes, said transverse pathway extending from a first axial end to a second axial end along a second central axis substantially orthogonal to the first central axis and intersecting with the first pathway at an intersection region; an electron source disposed proximate to one of the first and second axial ends of the second pathway for introducing a plurality of electrons along the second central axis such that said electrons travel through said transverse pathway toward said intersection region; one or more power sources for providing DC and RF voltages to said first and second sets of electrodes and to generate an electric field in each of the first and transverse pathways; a magnetic field source configured and adapted to generate a static magnetic field in a direction parallel to and on the second central axis; and a controller for controlling said DC and RF voltages applied to each of the first and second set of electrodes, said controller configured to generate an RF quadrupole field in the transverse pathway while the electron source introduces a plurality of electrons therealong such that at least a portion of the bandpass range of ions in the transverse pathway interact with the electrons to dissociate to form the ExD product ions.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the invention are described in detail, one skilled in the art will appreciate that the invention is not limited in its application to the details of construction, the arrangements of components, and the arrangement of steps set forth in the following detailed. The invention is capable of other embodiments and of being practiced or being carried out in various ways. Also, it is to be understood that the phraseology and terminology used herein is for the purpose of description and should not be regarded as limiting.

DETAILED DESCRIPTION OF EMBODIMENTS

Those skilled in the art will understand that the systems and methods described herein are non-limiting exemplary embodiments and that the scope of the applicants' disclosure is defined solely by the claims. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art. The features illustrated or described in connection with one exemplary embodiment may be combined with the features of other embodiments. Such modifications and variations are intended to be included within the scope of the applicants' disclosure.

Figure 1:
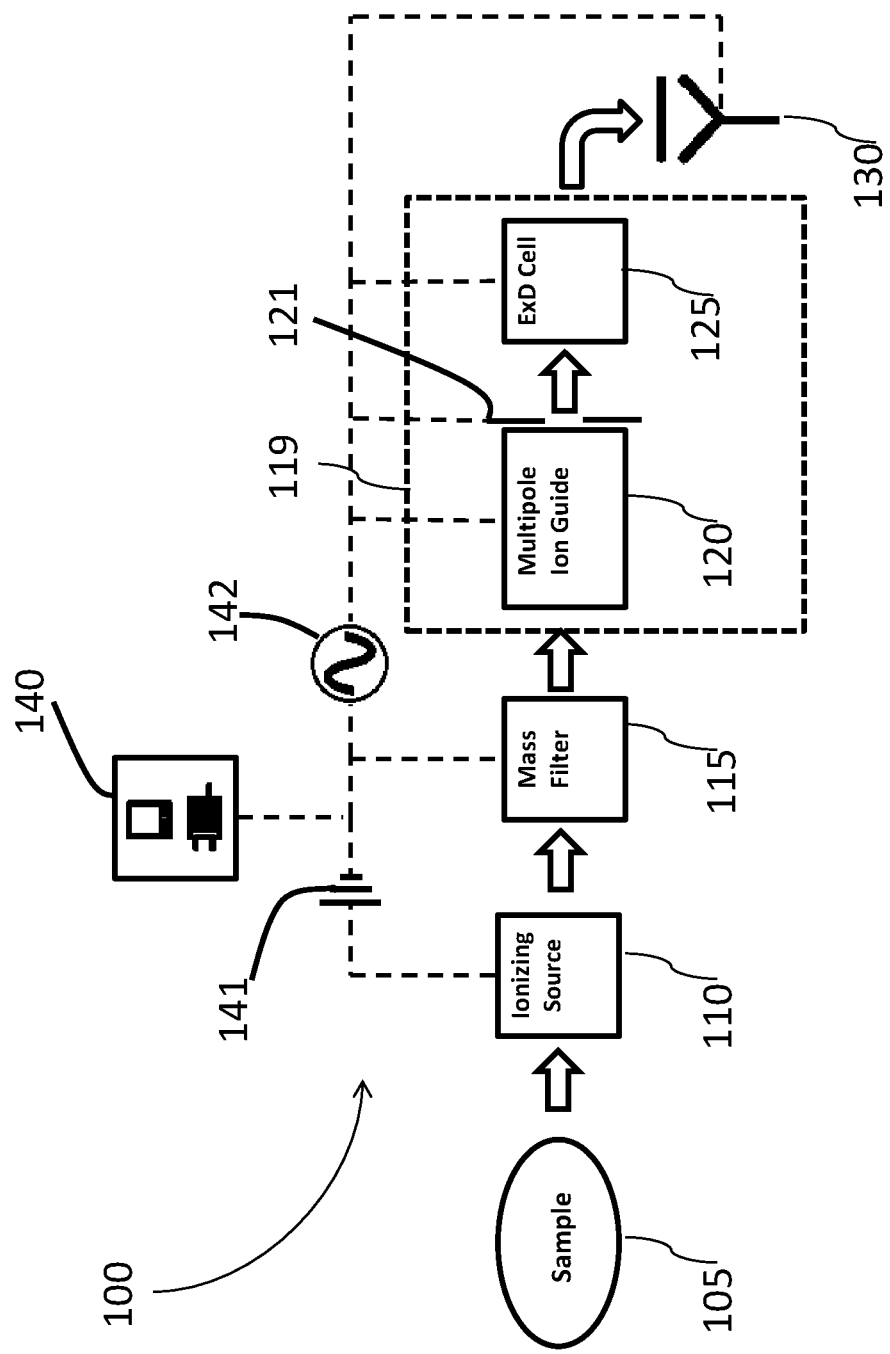
FIG. 1 depicts an exemplary apparatus according to an embodiment of the present teachings.

Referring now to FIG. 1, there is depicted an exemplary system 100 depicting an embodiment of the present teachings. A sample 105 containing or suspected to contain one or more glycopeptides that is to be characterized is ionized in an ionizing source 110 to make one or more glycopeptide ions. The ionizing source can be any source that is known in the art. In various embodiments, suitable ions sources can include, but should not be limited to, an electrospray ion source (ESI), an electron impact source and a fast atom bombardment source, an atmospheric pressure chemical ionization source (APCI), atmospheric pressure photoionization (APPI) source or a matrix assisted laser desorption source (MALDI). The ionization source can be chosen so as to preferably ionize glycopeptides. In a preferred method, electrospray ionization is utilized.

In some embodiments, the glycopeptides are ionized by alkali-metal charge reagents or alkali-earth metal charge reagents. As an example, the metal can be chosen from the group of ions which can include lithium, sodium, potassium, magnesium and calcium. In preferred embodiments, the metal cation is sodium. Sodiated glycans are generally more stable than protonated ones and as a result are especially preferred when performing glycan linkage analysis. Such sodiation can be performed by adding small quantities of Na+ ions as a salt to the glycopeptide solution. Examples of such added reagents can include sodium carbonate and sodium acetate.

After ionization, the glycopeptide ions are passed through to a mass filter 115. The mass filter functions as the first stage (Q1) in a tandem mass spectrometer system, with the system being modified in accordance with the teachings described herein. The mass filter 115 functions to remove ions that do not fit the criteria of having a predetermined m/z range thereby allowing only certain ions through to downstream processes. The mass filter 115 is traditionally a quadrupole filter that has RF and DC voltages applied to it and whose capability to filter ions is modeled by the Mathieu equation. While in preferred embodiments, the mass filter 115 comprises a set of quadrupole rods, it should be appreciated that the term mass filter is intended to cover any mass spectrometer type device that is capable of filtering ions to produce an effect of isolating ions. For example, the mass filter may comprise an ion trap device that traps ions and functions to scan out ions having certain m/z values. The mass filter may also comprise a Time-of-Flight (TOF) mass spectrometer which isolates ions having certain m/z values in a pulsed manner.

Once ions have been filtered, they enter a dissociation device in accordance with the teachings herein. The dissociation device 119 can comprise a multipole ion guide 120 and an ExD device 125 configured as described herein. In some embodiments, the multipole ion guide 120 may take the form of a quadrupole ion guide that operates in a manner similar to the Q2 region of a tandem mass spectrometer and operates as a collision cell. The collision cell is filled with a gas and is maintained at a high enough pressure and voltage so that multiple low energy collisions occur, which induces Collision Induced Dissociation (CID) of ions breaking parent ions into fragments. Depending on the energies provided to the collision cell and gases utilized, in certain embodiments of the invention, the multipole ion guide 120 operates to separate glycans from peptides, break peptides into fragments and/or break glycans into its component sugars.

The dissociation device 119 also comprises an ExD device 125, which accepts ions from the multipole ion 120 guide that acts as a collision cell and functions to react electrons with the incoming ions. In a preferred embodiment, the ExD device 125 is capable of operating as either an ExD device or an ion guide. When operating as an ion guide, ions that enter the ExD device 125 from the multipole ion guide 120 are passed through to the exit of the ExD device 125 without reactions. When operating the device as an ExD device 125, the electrons being utilized may range in energy from approximately 1 eV to 15 eV, depending on the type of electron associated dissociation reaction that is desired. Electron based reactions that take place in the ExD device 125 can function to generate peptide fragments, and perform cross-ring cleaving of glycans.

Between the multipole ion guide 120 and the ExD device 125 is disposed a lens electrode 121 configured to extract ions trapped by the multipole rod 120 through bandpass filtering. This bandpass filtering technique is described, for example, in PCT Published Application No. WO 2016/020789, incorporated by reference. The multipole rod set 120 is configured to receive a radial RF trapping voltage and/or a radial dipole DC voltage. The lens electrode 121 can be configured to receive an axial trapping AC voltage and/or a DC voltage. The bandpass range of ions can be extracted by applying a radial dipole DC voltage to the multipole rod 120 and a simultaneous axial trapping AC voltage to the lens electrode 121. Alternatively, a radial RF trapping voltage amplitude can be applied to the multipole rod set 120 and an axial trapping AC voltage can be simultaneously applied to the lens electrode 121.

Ions/fragments/ExD products that exit the ExD device 125 are then analyzed in a mass spectrometer 130. In several embodiments, the mass spectrometer 130 can be the final mass filter (Q3) consisting of a quadrupole filter and detector in a tandem mass spectrometer. In other embodiments, this last spectrometer may be a Time-of-Flight mass spectrometer or an ion trap. In preferred embodiments, this last stage is a TOF device.

As shown, the system 100 can additionally include a controller 140 operatively coupled to one or more of the elements of the system 100 so as to control the operation thereof. By way of example, the controller 140 can include a processor for processing information, data storage for storing mass spectra data, and instructions to be executed. As discussed in detail below and as generally known in the art and modified in accordance with the present teachings, the controller 140 can control the generation of ions by the ion source 110 and electrons by the electron source situated in the ExD cell 125 and/or to control the movement of ions and/or filtering of ions into and through the mass filter 115, the multipole ion guide 120, the lens electrode 121, the ExD cell 125 and the mass spectrometer 130 via the application of one or more RF/DC voltages to electrodes thereof, by way of example. It will be appreciated that though controller 140 is depicted as a single component, one or more controllers (whether local or remote) can be configured to cause the system 100 to operate in accordance with any of the methods described herein. Additionally, the controller 140 can also be operatively associated with an output device such as a display (e.g., a cathode ray tube (CRT) or liquid crystal display (LCD), for displaying information to a computer user) and/or an input device including alphanumeric and other keys and/or cursor control, for communicating information and command selections to the processor. Consistent with certain implementations of the present teachings, the controller 140 can execute one or more sequences of one or more instructions contained in data storage, for example, or read into memory from another computer-readable medium, such as a storage device (e.g., a disk). The one or more controller(s) can take a hardware or software form, for example, the controller 140 may take the form of a suitably programmed computer, having a computer program stored therein that may be executed to cause the system 100 to operate as otherwise described herein, though implementations of the present teachings are not limited to any specific combination of hardware circuitry and software. Various software modules associated with the controller 140, for example, can execute programmable instructions to perform the exemplary methods described below with reference to FIGS. 2, 3, 4, 5. The processor and associated other components may be utilized to display or interpret information received from the various other parts of the system 100. For example, the system may display mass spectra and/or ExD spectra that result from performing the methods and teachings utilizing the exemplary components that are described herein.

As shown in FIG. 1, the exemplary system 100 can additionally include one or more power supplies (e.g., DC power supply 141 and RF power supply 142) that can be controlled by the controller 140 so as to apply electric potentials with RF, AC, and/or DC components to electrodes of the various components to configure the elements of the system 100 in a coordinated fashion and/or for various different modes of operation, as discussed otherwise herein.

Figure 2:
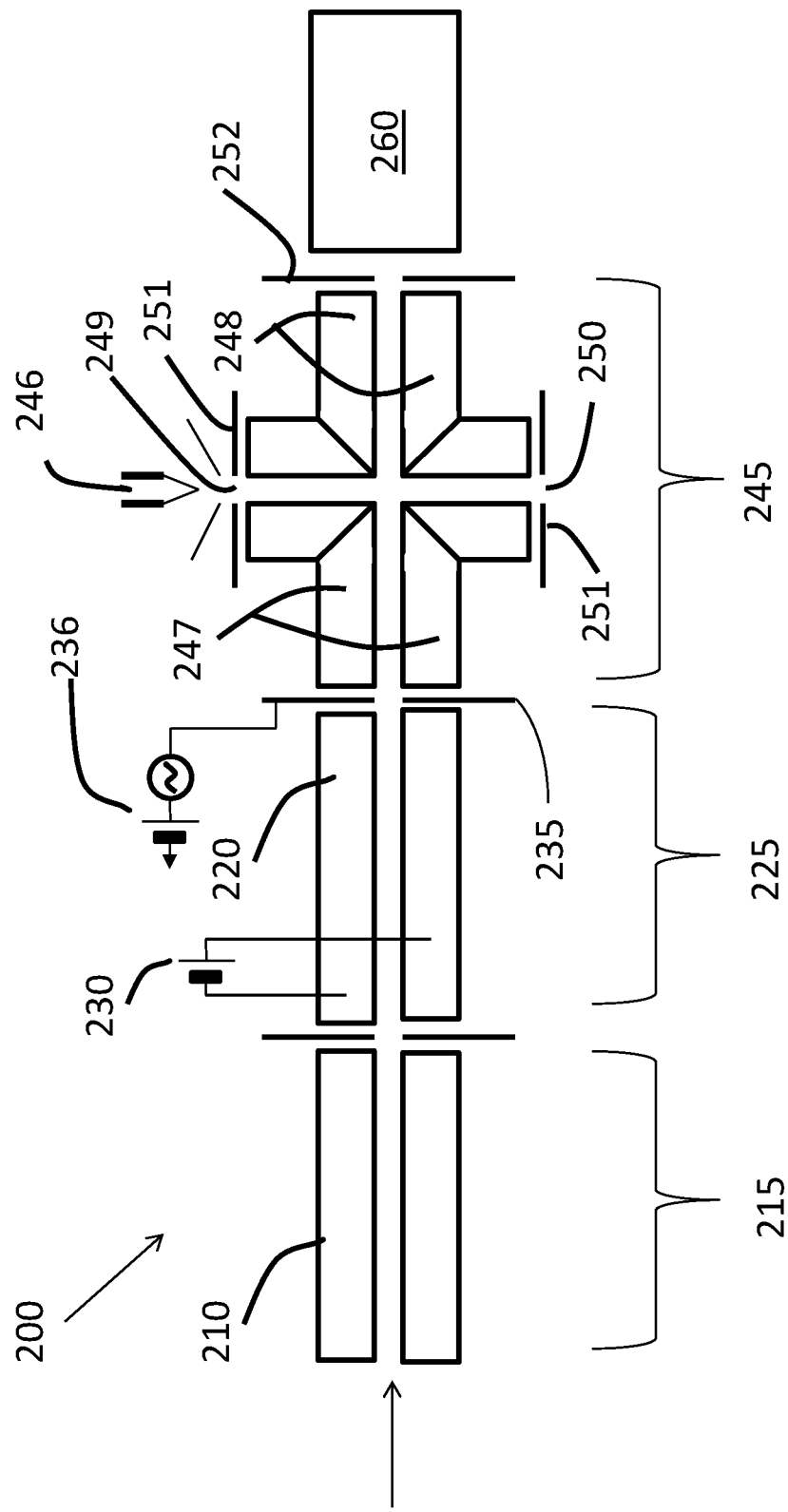
FIG. 2 depicts a more detailed cross sectional view of an exemplary embodiment of the present teachings.

Referring now to FIG. 2, there is depicted an embodiment of the present teachings that depicts a mass spectrometer system 200 which includes ions from an ion source (not shown) entering a first quadrupole 205 which operates as a mass filter. The first quadrupole 205 consists of a series of four rods 210 arranged in a quadrupole arrangement around a common axis. The quadrupole rods are attached to an RF source and a DC source (not shown). By selecting suitable RF and DC voltages according to the Mathieu equation, the motion of certain ions having characteristic m/z values can be made to pass through the quadrupole 205 in a stable trajectory while other ions are either made to be ejected radially from the quadrupole or made to contact the rods 210 where they are removed.

A second set of quadrupole rods 220 is disposed downstream of the first quadrupole 215. This second set of quadrupole rods 220 operates as a collision cell 225 and is attached to an RF voltage source and a dipole DC voltage source 230. Positioned downstream of the second set of quadrupole rods 220 is a lens filter 235 which has an AC voltage and DC voltage source 236 attached thereto. This second set of a quadrupole rods 220 can act as an ion guide allowing most ions to pass through unimpeded or alternatively, the second set of quadrupole rods 220 may be operated as a bandpass filter that can be operated by coupling of the RF voltage source and dipole DC voltage source to construct the bandpass filter in accordance with the present teachings in which ions having m/z ratios within a certain range are passed through.

Downstream of the lens filter 235 is disposed an ExD device 245. The ExD device 245 can be operated as an ion guide in which ions are passed through the device or as an ExD device where an electron source 236 introduces electrons to incoming ions along an orthogonal path to the ions so as to induce ECD, or ETD, etc. One exemplary embodiment of an ExD device 236 is depicted in PCT Published Application WO 2014/191821, published on Dec. 4, 2014, and incorporated by reference herein. The ExD device 245 comprises a first series of four L-shaped electrodes 247 arranged in a quadrupole arrangement around an ion path which partially defines a first pathway in which ions travel from the quadrupole ion guide (Only two of the four electrodes are depicted in FIG. 2). First portions of each of the four L-shaped electrodes which are generally parallel to one another function as quadrupole rods in the ExD cell 245. Second portions of each of the four L-shaped electrodes are generally perpendicular to the first portions and extend radially away from the ion path. Each of these four L-shaped electrodes is then mirrored across a plane tranverse to the ion path by a second set of L-shaped electrodes 248 (only two of which are depicted) that are spaced apart from the first set of L-shaped electrodes 247. Similar to the first set, each of the second set of L-shaped electrodes 248 has a first portion which are generally parallel to one another and parallel to the first portions of the first set of L-shaped electrodes. Together these first portions of the L-shaped electrodes partially define an ion guide and pathway for ions to traverse from the multipole ion guide 225 (eg. Quadrupole) to the mass analyzer 260. The second portions of the first 247 and second set 248 of L-shaped electrodes are also generally parallel to one another and define a second pathway that is substantially orthogonal to the first pathway. The second pathway offers a path for electrons to enter the ExD device 245. Each of the L-shaped electrodes is configured to receive an RF voltage signal from a suitable power source (not shown) that allows the generation of an RF field. The polarities of the RF voltages applied to adjacent L-shaped electrodes is opposite in field. This allows a defocusing of electrons as described in WO 2014/191821. The electrons are generated by an electron source 236, which can be a filament (tungsten, thoriated tungsten and others) or an electron emitter (Y2O3 cathode). As depicted in FIG. 2, the electron source 236 is disposed near one entrance 249 of the second pathway, however an alternative entrance 250 is also formed by the configuration of the ExD device herein described. An additional electron source may be positioned at this alternative entrance 250. Gating electrodes 251 are also positioned at these entrances to control entrance and/or exit of electrons/ions. A magnet (not shown) is positioned in the ExD device 245 that generates a static magnetic field in the ExD device that is substantially parallel to and on the second pathway (eg., along the path of the electrons).

A gating electrode 252 is positioned at the exit of the first pathway of the ExD cell 245 to control the exit of ions from the ExD device. Positioned downstream of the ExD device and gating electrode is a mass spectrometer system 260 (eg. Quadrupole, TOF, trap, etc.).

Figure 3A:
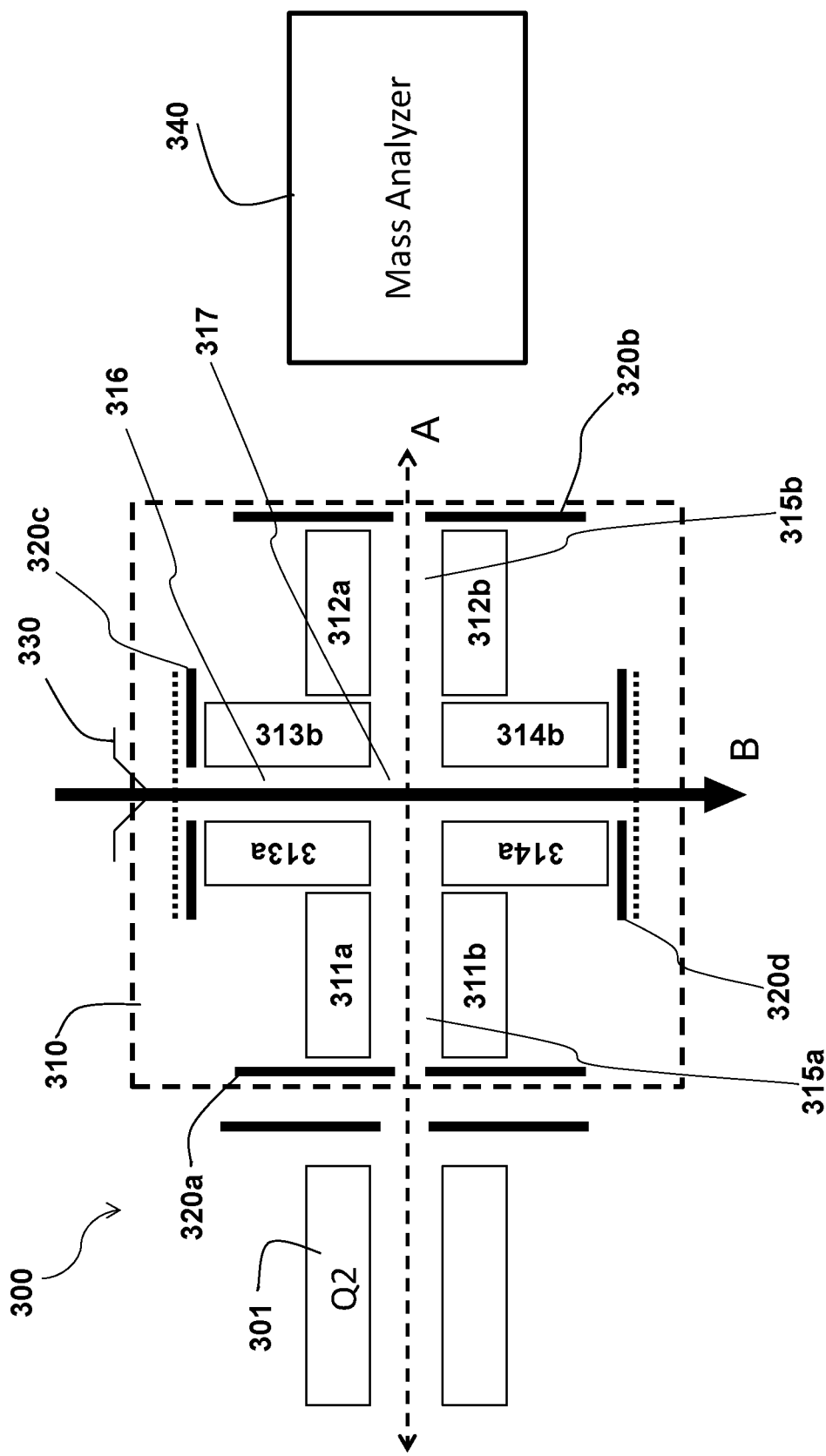
FIG. 3A depicts a cross sectional view of the configuration of an exemplary ExD device used in an embodiment of the present teachings.

With reference now to FIG. 3A, a partial view of an exemplary system 300 and a schematic for performing the exemplary method of FIG. 1 in accordance with various aspects of the present teachings are depicted. As best shown in FIG. 3A, the system 300 generally includes an electron source 330 and an ExD cell 310 having a plurality of electrodes that are arranged so as to define a central longitudinal axis (A) and a transverse axis (B). As shown, the system 300 can additionally include an upstream quadrupole rod set Q2 301 acting as a collision cell (disposed between a mass filter (not shown) and the ExD cell 310) and a downstream quadrupole rod set Q3 (disposed between the ExD cell 310 and a detector) operating as a mass analyzer 340. In various aspects, the ExD cell 310 can be housed within a chamber (e.g., at sub-atmospheric pressures), with a gas such as helium (He) or nitrogen (N2) being added to slow the precursor ions' movement within the ExD cell 310 so as to lengthen the interaction time between the ions and the electrons within the interaction region. Typically, the pressure of the cooling gas can be between $10^{-2}$ to $10^{-4}$ Torr, by way of non-limiting example. In some embodiments, the ExD cell 310 and the collision cell Q2 301 are housed together in a low pressure chamber and are at substantially the same pressure. Additionally, a magnetic field source (not shown), such as a permanent magnet can be configured to generate a static magnetic field that is parallel to and on the transverse passage 316, as depicted schematically for example by the arrow (B). The magnetic field can also be generated by any other magnetic field generating source and can also include an electromagnetic, a neodymium magnet, or the like that functions to generate a field parallel to and in line with the second central axis (B) of the second pathway. The magnetic flux density can be any density able to implement the magnetic field to cause focusing of an electron beam and can range, for example, up to 1.5 T, but preferably about 0.1 to 1.0 T. Magnets with higher density can be positioned further away from the electrode pair. A magnetic field (as indicated by the arrow B) of 0.1 T is aligned to be parallel to and along the path of electron direction.

Figure 3B:
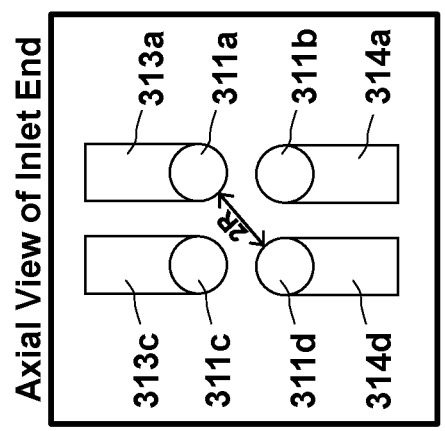
FIG. 3B depicts an exemplary embodiment of the axial end of an ExD device in an embodiment of the present teachings.

Unlike the continuous L-shaped electrodes (247,248) depicted in FIG. 2, the ExD cell 310 comprises multiple sets of electrodes that together define the axial passage and the transverse passage. Specifically, FIG. 3A depicts electrodes 311a-d (only 311a and b being depicted in FIG. 3A, but more fully depicted in FIG. 3B) being electrically isolated from and forming a general L-shape with one of the adjacent electrodes from the third (313a, 313c) and fourth sets (314a, 314d) as shown in FIG. 3B such that the signals applied thereto can differ from one another during the exemplary methods described above. As should be appreciated, to form the continuous L-shaped electrode as depicted in FIG. 2, the electrode pairs (311a/313a, 311b/314a, 311d/314d, 311c/313c) are joined. That is, the portion of the electrode 311a, for example, that extends along the central longitudinal axis and the portion of the electrode 313a that extends along the transverse axis are always maintained at the same potential. By this arrangement and with the proper application of RF voltages (e.g., a sinusoidal RF potential with the phase of each adjacent electrode within and between sets 311d,314d being opposite to one another), a quadrupole field can be generated in each of the axial and transverse passages.

As shown in FIG. 3A, the exemplary ExD cell 310 comprises 4 sets of electrodes 311-314, each of which is arranged in a quadrupole orientation about one of the two axes. That is, each set of electrodes 311-314 comprise four parallel conductive rods or elongated electrodes arranged such that their centers form the corners of a square and whose opposing poles can be electrically connected (e.g., for a typical quadrupole field a superposition of a static DC potential and a sinusoidal RF potential with the phase of adjacent electrodes being opposite to one another). Specifically, as shown in FIG. 3A, a first set 311 of four electrodes 311a-d are disposed about the central longitudinal axis (A) so as to define a portion 315a of an axial passageway. The first set 311(a-d) of electrodes extend axially therealong from an inlet end through which precursor ions generated by an upstream sample ion source (not shown, e.g., via Q1 and Q2) can be received to a distal end within the ExD cell 310. A second set 312 of four electrodes 312a-d (of which only electrodes 312a and 312b are shown) are also disposed about the central longitudinal axis (A) so as to define a second portion 315b of the axial passageway. As shown, the second set 312 of electrodes are spaced apart from the first set 311 of electrodes such that the transverse axis (B) extends between the distal end of the first set 311 of electrodes and the proximal end of the second set 312 of electrodes. As shown, the second set 312 of electrodes extend from the proximal end to a distal end through which ions can be ejected from the ExD cell 310 to one or more mass analyzers 340 (e.g., Q3 via exit lens IQ3A 320b) or a detector, for example. Additionally, a third set 313 of electrodes 313a-d and fourth set of 314 of electrodes 314a-d (in each set only two of the four electrodes are shown) are disposed about the transverse axis (B), with each set being disposed about in a quadrupole orientation on opposite sides of the central longitudinal axis (A). By this arrangement, each electrode of the first set 311 generally forms an L-shape with one of the electrodes of the third set 313 or fourth set 314, while each electrode of the second set 312 generally forms an L-shape with an electrode of the third set 313 or fourth set 314. Thus, as shown, the first and second sets 311, 312 at least partially define the axial passageway and the third and fourth sets 313, 314 at least partially define a transverse passage 316 that intersects with the axial passageway 315 at an intersection region 317.

It will be appreciated by those skilled in the art that the electrodes of the first, second, third, and fourth sets can have a variety of shapes and sizes but are generally configured to generate a quadrupole field within the portion of the passageway each set surrounds when an appropriate RF signal is applied to the electrodes of each set. By way of non-limiting example, each electrode can have a longitudinal dimension (e.g., a dimension along the central longitudinal axis (A) for electrodes 311a-d and along the transverse axis (B) for electrodes 313a-d) in a range of about 3 cm, and a transverse dimension (e.g., a width or radius, a dimension perpendicular to the central longitudinal axis (A) for electrodes 311a-d and perpendicular to the transverse axis (B) for electrodes 313a-d) in a range of about 5 mm or greater. As shown in FIG. 3B, in some aspects, each electrode can be radially separated from its opposed electrode in that set (e.g., the non-adjacent electrode across the central longitudinal axis (A) for each electrode 311a-d) by a distance (2R), where R is in a range of about 2 mm to about 10 mm.

With continued reference to FIG. 3A, the ExD cell 310 can further include a plurality of lenses 320a-d, each of which can be in the form of a conductive plate having a central orifice through which ions or electrons can be transmitted. As shown, the lenses 320a-d can be disposed in proximity to the inlet or outlet ends of the various sets of electrodes discussed above. For example, lens 320a can function as an ion injection port through which ions can enter the ExD cell and lens 320b can function as the ion ejection port through which ions (e.g., product ions as discussed below) can exit the ExD cell 310 after dissociation. As discussed otherwise herein, RF and/or DC potentials can be applied to the various lenses 320a-d for controlling the movement of ions within the ExD cell 310. For example, as discussed in more detail below, various RF and/or DC signals can be applied to lenses 320a and 320b during various phases of ion processing to facilitate axial trapping of the ions within portions of the space between the electrodes or to facilitate the injection and ejection of ions into and out of the ExD cell 310. Similarly, lens 320c and lens 320d can be biased (e.g., via application of an appropriate DC voltage) to block the exit of the ions within the transverse pathway 316.

In various aspects of the present teachings, Q1 can be operated as a conventional transmission RF/DC quadrupole mass filter operative to select an ion of interest and/or a range of ions of interest. By way of example, the quadrupole rod set Q1 can be provided with RF/DC voltages suitable for operation in a mass-resolving mode. As will be appreciated by a person skilled in the art, taking the physical and electrical properties of Q1 into account, parameters for an applied RF and DC voltage can be selected so that Q1 establishes a quadrupole field having an m/z passband selected to allow particular precursor ions (e.g., exhibiting an m/z falling within a particular range) to traverse the quadrupole field largely unperturbed, while ions having m/z ratios falling outside the passband can be degenerated by the quadrupole field into orbital decay. It should be appreciated that this mode of operation is but one possible mode of operation for Q1. In some embodiments, a set of RF-only stubby rods can be provided between neighboring pairs of quadrupole rod sets to facilitate the transfer of ions between quadrupoles. The stubby rods can serve as a Brubaker lens and can help prevent ions from undergoing orbital decay due to interactions with any fringing fields that may have formed in the vicinity of an adjacent lens, for example, if the lens is maintained at an offset potential. Similarly, ions (e.g., product ions) that are transmitted by the ExD cell 310 can pass into the adjacent quadrupole rod set Q3, which can be bounded upstream by lens 320b. As will be appreciated by a person skilled in the art, Q3 can be operated in a number of manners, for example as a scanning RF/DC quadrupole, as a quadrupole ion trap, or as a linear ion trap.

Figure 4:
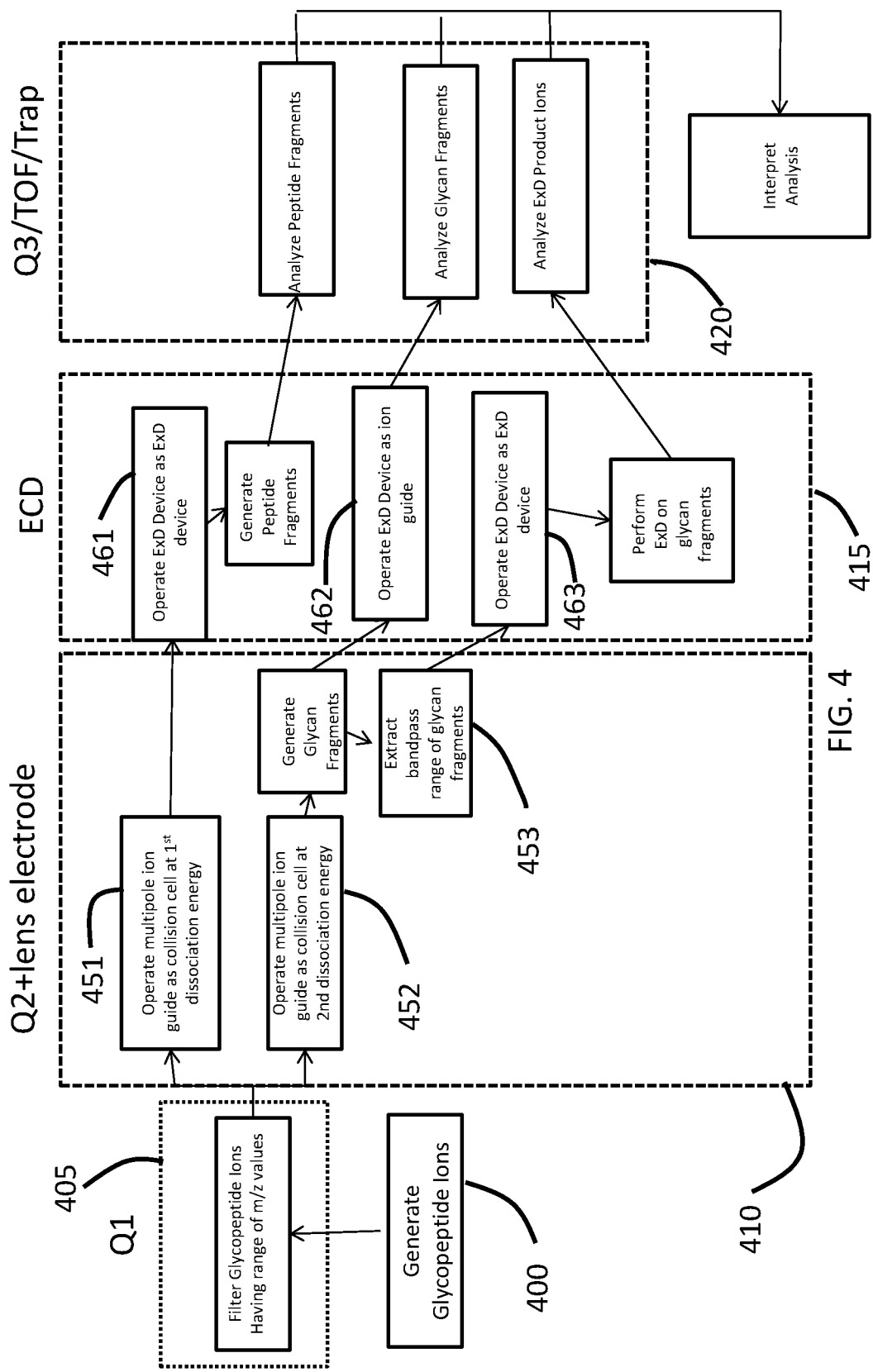
FIG. 4 depicts a flowpath of a method used to characterize a glycopeptide in an exemplary embodiment of the present teachings.
Figure 5:
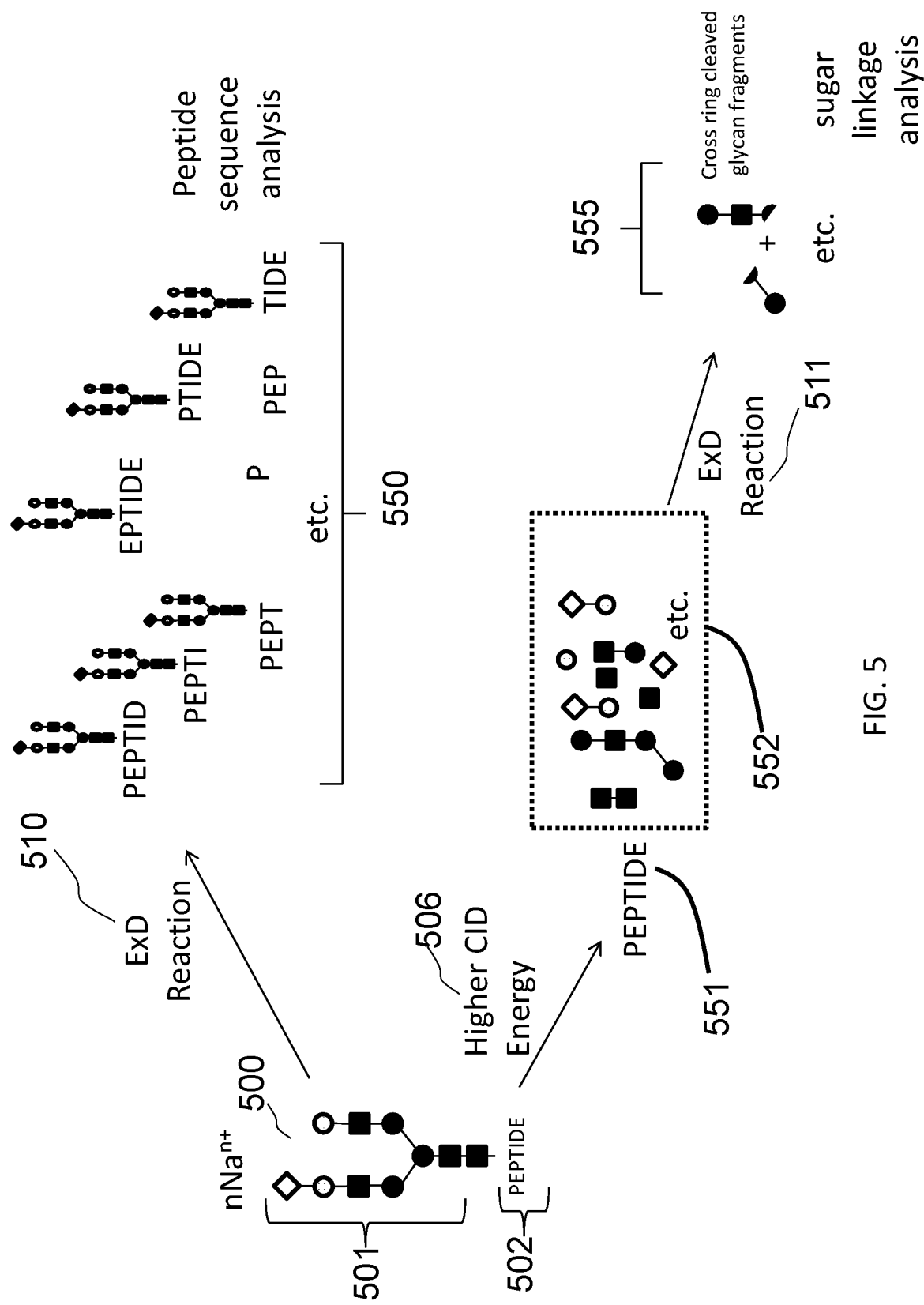
FIG. 5 depicts an exemplary cascade of fragments obtained from a glycopeptide according to an embodiment of the present teachings.

The within described teaching may be utilized to characterize a glycopeptide ion in a single experimental run, that is the glycopeptide peptide sequence, the glycan composition, and glycan bonding chains can be obtained in an analysis using the within described procedure by configuring the system to operate in differing manners as described herein Referring now to FIGS. 4 and 5, there is depicted a flowchart demonstrating the operation of the within described procedure and/or system to carry out one embodiment of the present teachings.

In box 400, glycopeptide analytes, preferably that have been sodiated are subjected to ionization using a suitable ionization process. The ionized species pass through Q1 405, e.g., a first mass filter, which separates ions having characteristic m/z values. This can include a range of m/z values, but in preferred embodiment, a single glycopeptide ion having a characteristic m/z value is isolated in the first mass filter with all other ion types being ejected radially or otherwise being removed from Q1. Isolated glycopeptides then pass through to Q2 410, e.g., a quadrupole collision cell modified in accordance with the present teachings, which operates in a number of different modes so as to perform various operations on the filtered glycopeptide ions received from Q1 405.

In one such mode, the quadrupole collision cell 410 is operated in a first mode 451 as a collision cell at a first dissociation energy. This first dissociation energy involves sufficiently mild conditions that collision induced dissociation of the glycopeptides is performed to form peptide fragments. In another mode 452, the quadrupole collision cell 410 is operated as a collision cell at a second dissociation energy, wherein the second dissociation is higher than the first dissociation energy. This second dissociation energy operates at harsher conditions that causes the collision induced dissociation of the glycopeptides to form glycan fragments. In yet another mode 453, a lens electrode, positioned at the exit of the quadrupole collision cell 410 is configured in such a way to simultaneously apply a radial dipole DC voltage to the quadrupole rod set that makes up the quadrupole collision cell 410 and an axial trapping AC voltage to the lens electrode. Alternatively one can simultaneously apply a radial RF trapping voltage amplitude to the quadrupole rod set and an axial trapping AC voltage to the lens electrode. In these modes, the combination of the action of the quadrupole rod set and the exit lens operate as a secondary filter to extract a bandpass range of fragments having particular m/z values without the need to incorporate an additional mass filter. In particular, this operates to selective extract ranges of glycan fragments from the quadrupole collision cell.

Ions removed from the quadrupole collision cell 410 that have passed through the lens electrode, enter an ExD device 415 that is described in more detail, elsewhere in the present teachings. The ExD device 415 operates in a number of different modes. Depending on the number and type of ions, the ExD device 415 can be operated in two modes. In the first mode 462, the ExD device operates as an ion guide which transfers ions from the quadrupole collision cell 410 downstream for processing/detection or in the second mode 461/463, the ExD device perform an electron based dissociation of the incoming ions. The functioning of these modes is for the purpose of interrogating various features of the original glycopeptide molecule as set forth herein.

When used as in ExD device, in a first ExD mode 461, peptide fragments that have been generated while operating the quadrupole collision cell 410 at the first dissociation energy 451 are reacted with electrons which causes fragmentation of the peptide fragments in such a manner that c and z fragments are created. This allows the peptide sequence, sites of glycoslation on the peptide chain and glycan mass to be identified. In a second ExD mode 463, the extracted bandpass range of glycan fragments that are created when operating the quadrupole collision cell 410 at the second dissociation energy 452 to create glycan fragments can be subjected to an ExD process. ExD performed on these fragments at selected conditions cross cleaves glycan rings of the glycan fragments to generate additional glycan fragments that allow the interrogation of the glycan linkage positions on the monosaccharides that make the fragments.

When used as an ion guide in mode 462, the ExD device passes ions that have been generated in the quadrupole collision cell 410 to the mass spectrometer 420 (eg. Q3/TOF/Trap) for detection and analysis. In this manner, glycan fragments generated in the quadrupole collision cell comprise glycan chains having one or more component sugars. Mass analyzing these chains can provide a determination of overall mass of the component sugars which allows a determination of the overall structure of the glycans. Specific linkages of the glycan structure are determined in accordance with the ExD analysis described previously.

The generated peptide fragments and glycan fragments are then mass analyzed in a suitable mass spectrometer 420. This can be performed by using any methods that are known in the art and can include a detector that is coupled with a quadrupole filter, time of flight mass spectrometer, or ion trap. In other embodiments, one or more additional processing steps can be incorporated in the methods described herein for the purpose of transferring ions between the various stages.

Now referring to FIG. 5, a depiction of the various processes that a glycopeptide molecule undergoes utilizing the methods and apparatus of the present teachings is shown. Glycopeptide 500, optionally sodiated, comprises a glycan 501 portion and a peptide 502 portion. Subjecting the glycopeptide 500 to lower energy dissociation energy 505 in the quadrupole collision cell in which minimal or no CID occurs in which glycopeptide ions are passed through to ECD device. In alternative embodiments, minimal dissociation energy is applied and the quadrupole collision cell operates as an ion guide. The glycopeptide ions pass through to the ECD device that selectively cleaves peptide fragments in various ways by way of ExD reactions that generate c and z fragments 550 of the original peptide 502. These fragments 550 when processed by a processor can be used to sequence the order of the peptide 502. The lower energy 505 collision induced disassociation also produces a relatively intact glycan portion 501 that can be used to provide an overall mass of the glycan portion and an estimate of individual components of the glycan part 501.

When subjected to higher CID energy 506 (eg. higher than the energy utilized in the peptide sequence analysis), the original glycopeptide 500 is caused to fragment into component parts. The peptide portion 502 generates a relatively intact peptide fragment 551 that may be used to sequence the peptide chain using a process similar to the ExD reaction 510. The glycan portion 501 under the higher CID energy 506 fragments into glycan fragments 552 that may consist of individual glycan monosaccharide units or sub-chains of the original glycan 501. The glycan fragments 552 that are created after CID process 506 may be selected utilizing a bandpass filter in accordance with the present teachings and transmitted to an ExD device where the glycan is subject to an ExD reaction 511 that performs cross-ring cleavage dissociation on individual glucose units on the smaller glycan chains to form cross-ring glycan fragment parts 555. The mass analysis of these fragment parts 555 can be utilized to sequence the monosaccharides and more particularly, the cross-ring cleavage fragments allows a determining of ring linkages (ie, what position on a particular monosaccharide is linked to its neighbor) which can be utilized to interrogate the structure of the original glycan molecule. In another embodiment, the glycan portion 501 that results from the use of either the lower or the higher CID energy 506 can be selected utilizing a bandpass filter and then passed through an ExD device that functions solely as an ion guide. In this manner, ions that are specifically the intact glycan pass through to be mass analyzed and its analysis provides a measure of the overall mass of the glycan structure. As the glycan structure can be assumed to be a simple combination of the component sugars, an estimated reconstruction of the rough structure of the glycan portion can be carried out by a processor.

More efficient ExD reactions can be performed by utilizing a quasi-flow through method in which ions travelling through the ExD device are momentarily trapped in the device to prolong their exposure to electrons. The ExD device exit lens can oscillate between a closed position and an open position so that in one mode, ions begin to accumulate in the ExD device that allows increased exposure time to the electrons and in a second mode, in which the exit lens is opened and ions are ejected from the device through the exit gate. In alternative embodiments, an lens at the ion entrance end of the ExD device may also open and close so as to control the influx of ions into the ExD device. An example of this is exemplified in WO 2014/191821, which is incorporated by reference, herein.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for mass spectrometer analysis comprising:
a first quadrupole mass filter;
a multipole rod set of an ion guide to receive ions from the first quadrupole mass filter, the multipole rod set adapted to receive a radial radio frequency (RF) trapping voltage and a radial dipole direct current (DC) voltage,
a lens electrode of the ion guide positioned at one end of the multipole rod set to extract ions trapped by the multipole rod set and adapted to receive an axial trapping alternating current (AC) voltage and a DC voltage,
an ExD device adapted to perform electron capture dissociation or electron transfer dissociation, the ExD device being positioned so that an entrance of the ExD device is disposed on the other side of the lens electrode opposite the multipole rod set,
a mass analyzer positioned at an exit of the ExD device for receiving ions from the ExD device,
a processor in communication with the multipole rods set and the lens electrode that simultaneously applies a radial dipole DC voltage to the multipole rod set and an axial trapping AC voltage to the lens electrode or simultaneously applies a radial RF trapping voltage amplitude to the multipole rode set and an axial trapping AC voltage to the lens electrode in order to extract a bandpass mass range of ions trapping in the multipole rod set.

2. The system of claim 1 wherein the mass analyzer comprises a time-of flight mass spectrometer.

3. The method of claim 2 wherein the metalizing comprises reacting the glycopeptides with a sodium salt.

4. The system of claim 1 wherein the mass analyzer comprises an ion trap.

5. The system of claim 1 wherein the mass analyzer comprises a second quadrupole mass filter.

6. The system of claim 1 wherein said ExD device operates in at least one of two modes, wherein in one mode the ExD device functions as an ion guide and wherein in the second mode, the ExD device performs electron capture dissociation or electron transfer dissociation.

7. The system of claim 6 wherein said ExD device comprises:
a first set of electrodes at least a first segment of which is arranged in a quadrupole orientation about a first central axis, wherein said first segment of the first set of electrodes extends axially along said first central axis from a proximal inlet end to a distal end so as to define a first portion of a first pathway extending along said first central axis, said proximal inlet end for receiving the bandpass range of ions from the exit end of the ion guide;

a second set of electrodes at least a first segment of which is arranged in a quadrupole orientation about the first central axis so as to define a second portion of the first pathway, wherein said first segment of the second set of electrodes extends axially along said first central axis from a proximal end to a distal outlet end, the proximal end of the second set of electrodes being spaced apart from the distal end of the first set of electrodes such that a transverse pathway extends between the proximal end of the second set of electrodes and the distal end of the first set of electrodes, said transverse pathway extending from a first axial end to a second axial end along a second central axis substantially orthogonal to the first central axis and intersecting with the first pathway at an intersection region;

an electron source disposed proximate to one of the first and second axial ends of the second pathway for introducing a plurality of electrons along the second central axis such that said electrons travel through said transverse pathway toward said intersection region;

one or more power sources for providing DC and RF voltages to said first and second sets of electrodes and to generate an electric field in each of the first and transverse pathways;

a magnetic field source configured and adapted to generate a static magnetic field in a direction parallel to and on the second central axis; and a controller for controlling said DC and RF voltages applied to each of the first and second set of electrodes, said controller configured to generate an RF quadrupole field in the transverse pathway while the electron source introduces a plurality of electrons therealong such that at least a portion of the bandpass range of ions in the transverse pathway interact with the electrons to dissociate to form the ExD product ions.

8. The method of claim 1 wherein ionizing the sample to form glycopeptide ions comprises metalizing the one or more glycopeptides.

9. The method of claim 1, wherein the extracting a bandpass range of ions is performed by simultaneously applying a radial dipole DC voltage to the multipole rod set and axial trapping AC voltage to the lens electrode and the radial dipole DC voltage and the AC voltage are selected so as to extract only glycan fragments having a range of pre-selected m/z values.

10. The method of claim 1, wherein the extracting a bandpass range of ions is performed by simultaneously applying a radial RF trapping voltage amplitude to the multipole rod set and an axial trapping AC voltage to the lens electrode and the RF trapping voltage amplitude and the AC voltage are selected so as to extract only glycan fragments having a range of pre-selected m/z values.

11. The method of claim 1 wherein the ExD comprises:
a first set of electrodes at least a first segment of which is arranged in a quadrupole orientation about a first central axis, wherein said first segment of the first set of electrodes extends axially along said first central axis from a proximal inlet end to a distal end so as to define a first portion of a first pathway extending along said first central axis, said proximal inlet end for receiving the bandpass range of ions from the exit end of the ion guide;

a second set of electrodes at least a first segment of which is arranged in a quadrupole orientation about the first central axis so as to define a second portion of the first pathway, wherein said first segment of the second set of electrodes extends axially along said first central axis from a proximal end to a distal outlet end, the proximal end of the second set of electrodes being spaced apart from the distal end of the first set of electrodes such that a transverse pathway extends between the proximal end of the second set of electrodes and the distal end of the first set of electrodes, said transverse pathway extending from a first axial end to a second axial end along a second central axis substantially orthogonal to the first central axis and intersecting with the first pathway at an intersection region;

an electron source disposed proximate to one of the first and second axial ends of the second pathway for introducing a plurality of electrons along the second central axis such that said electrons travel through said transverse pathway toward said intersection region;

one or more power sources for providing DC and RF voltages to said first and second sets of electrodes and to generate an electric field in each of the first and transverse pathways;

a magnetic field source configured and adapted to generate a static magnetic field in a direction parallel to and on the second central axis; and a controller for controlling said DC and RF voltages applied to each of the first and second set of electrodes, said controller configured to generate an RF quadrupole field in the transverse pathway while the electron source introduces a plurality of electrons therealong such that at least a portion of the bandpass range of ions in the transverse pathway interact with the electrons to dissociate to form the ExD product ions.

12. The method of claim 1 wherein the ExD comprises:
a first set of electrodes at least a first segment of which is arranged in a quadrupole orientation about a first central axis, wherein said first segment of the first set of electrodes extends axially along said first central axis from a proximal inlet end to a distal end so as to define a first portion of a first pathway extending along said first central axis, said proximal inlet end for receiving the bandpass range of ions from the exit end of the ion guide;

a second set of electrodes at least a first segment of which is arranged in a quadrupole orientation about the first central axis so as to define a second portion of the first pathway, wherein said first segment of the second set of electrodes extends axially along said first central axis from a proximal end to a distal outlet end, the proximal end of the second set of electrodes being spaced apart from the distal end of the first set of electrodes such that a transverse pathway extends between the proximal end of the second set of electrodes and the distal end of the first set of electrodes, said transverse pathway extending from a first axial end to a second axial end along a second central axis substantially orthogonal to the first central axis and intersecting with the first pathway at an intersection region;

an electron source disposed proximate to one of the first and second axial ends of the second pathway for introducing a plurality of electrons along the second central axis such that said electrons travel through said transverse pathway toward said intersection region;

one or more power sources for providing DC and RF voltages to said first and second sets of electrodes and to generate an electric field in each of the first and transverse pathways;

a magnetic field source configured and adapted to generate a static magnetic field in a direction parallel to and on the second central axis; and a controller for controlling said DC and RF voltages applied to each of the first and second set of electrodes, said controller configured to generate an RF quadrupole field in the transverse pathway while the electron source introduces a plurality of electrons therealong such that at least a portion of the bandpass range of ions in the transverse pathway interact with the electrons to dissociate to form the ExD product ions.

13. A method of analyzing a sample containing one or more glycopeptides, the method comprising:
    ionizing the sample to form glycopeptide ions,
    isolating one or more glycopeptide ions in a mass filter,
    fragmenting the isolated glycopeptide ions in a multipole rod set of an ion guide, the multipole rod set having an entrance end and an exit end, the entrance end receiving fragmented glycopeptide ions from the mass filter, the multipole rod set adapted to receive a radial radio frequency (RF) trapping voltage and a radial dipole direct current (DC) voltage, the ion guide having a lens electrode positioned at the exit end of the multipole rod set to extract ions trapped by the multipole rod set and adapted to receive an axial trapping alternating current (AC) voltage and a DC voltage,
    extracting a bandpass range of ions of the fragmented glycopeptide ions from the exit end of the ion guide into an ExD device by simultaneously applying a radial dipole DC voltage to the multipole rod set and axial trapping AC voltage to the lens electrode or simultaneously applying a radial RF trapping voltage amplitude to the multipole rod set and an axial trapping AC voltage to the lens electrode
    performing an electron dissociation reaction or electron transfer reaction of the bandpass range of ions in the ExD device to form ExD product ions,
    mass analyzing the ExD product ions.

14. A method of analyzing a glycopeptide in a sample comprising:
    providing a mass filter,
    providing a multipole rod set of an ion guide
    providing an ExD device positioned downstream of the multipole rod set, the ExD device adapted to operate in at least one of two modes, wherein in one mode the ExD device functions as an ion guide and wherein in the second mode, the ExD device performs electron capture dissociation or electron transfer dissociation,
    providing a mass analyzer positioned downstream of the ExD device
    providing a lens electrode positioned between the multipole rod set and the ExD device
    ionizing the sample to form metallized sample ions,
    transmitting the metallized sample ions to the mass filter,
    operating the mass filter to selectively transmit glycopeptide ions having a preselected m/z range into the multipole rod set of an ion guide,
    configuring the multipole rod set to operate as a collision cell with the collision cell operating at a first dissociation energy to cause formation of peptide fragments, and configuring the ExD device to operate as an ion guide, so as to transmit the formed peptide fragments through the ExD device to the mass analyzer, and analyzing the peptide fragments in the mass analyzer,
    configuring the multipole rod set to operate as a collision cell at a second dissociation energy to cause the formation of glycan fragments, the second dissociation energy being higher than the first dissociation energy, and configuring the ExD device to operate as an ion guide, so as to transmit the formed glycan fragments through the ExD device to the mass analyzer, and analyzing the glycan fragments in the mass analyzer,
    extracting a bandpass range of glycan fragment ions from the multipole rod set into the ExD device by simultaneously applying a radial dipole DC voltage to the multipole rod set and axial trapping AC voltage to the lens electrode or simultaneously applying a radial RF trapping voltage amplitude to the multipole rod set and an axial trapping AC voltage to the lens electrode, the bandpass range of glycan fragments being defined by a pre-selected range of m/z values and configuring the ExD device to operate as an electron transfer reaction device or electron dissociation device, and performing an ExD reaction on the bandpass range of glycan fragment ions to form ExD product ions, and
    mass analyzing the ExD product ions.

* * * * *